United States Patent
Archibald et al.

[11] 4,034,098
[45] July 5, 1977

[54] SULPHONAMIDOPIPERIDYL DERIVATIVES

[75] Inventors: John Leheup Archibald, Windsor; John Lambert Jackson, Royston, both of England

[73] Assignee: John Wyeth & Brother Limited, Maidenhead, England

[22] Filed: Nov. 24, 1975

[21] Appl. No.: 634,567

[30] Foreign Application Priority Data

Dec. 11, 1974 United Kingdom ............ 53643/74

[52] U.S. Cl. .................... 424/267; 260/293.61; 260/293.73
[51] Int. Cl.² ................................ C07D 211/56
[58] Field of Search ............ 260/293.73; 424/267

[56] References Cited
UNITED STATES PATENTS 3,341,584  9/1967  Larsen et al. ..................... 260/556

Primary Examiner—Cecilia M. S. Jaisle

[57] ABSTRACT

This invention relates to compounds having the general formula:

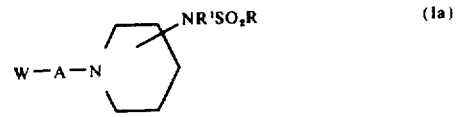

wherein W represents a phenyl or indolyl radical, either of which radicals may be unsubstituted or substituted by halogen, lower alkyl, lower alkoxy or hydroxy. A represents a lower alkylene radical, an oxo lower alkylene radical or a hydroxy lower alkylene radical; R represents a phenyl radical optionally substituted by halogen, lower alkyl, lower alkoxy or hydroxy, a cycloalkyl radical of 5 to 7 carbon atoms or a lower alkyl radical; $R^1$ represents hydrogen or a lower alkyl radical or a pharmaceutically acceptable acid addition or quaternary ammonium salt thereof; which possess hypotensive activity.

6 Claims, No Drawings

SULPHONAMIDOPIPERIDYL DERIVATIVES

This invention relates to novel sulphonamido derivatives, to processes for preparing them and to pharmaceutical compositions containing them.

The invention provides a compound having the general formula:

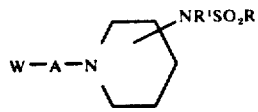
(Ia)

wherein W represents a phenyl or indolyl radical, either of which radicals may be unsubstituted or substituted by halogen, lower alkyl, lower alkoxy or hydroxy; A represents a lower alkylene radical, an oxo lower alkylene radical or a hydroxy lower alkylene radical; R represents a phenyl radical optionally substituted by halogen, lower alkyl, lower alkoxy or hydroxy, a cycloalkyl radical of 5 to 7 carbon atoms or a lower alkyl radical; R¹ represents hydrogen or a lower alkyl radical; or a pharmaceutically acceptable acid addition or quaternary ammonium salt thereof.

The compounds of formula Ia form part of a general class of novel sulphonamido derivatives having the general formula

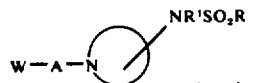
(I)

wherein W represents a phenyl or indolyl radical, either of which radicals may be unsubstituted or substituted by halogen, lower alkyl, lower alkoxy or hydroxy. A represents a lower alkylene radical, an oxo lower alkylene radical or a hydroxy lower alkylene radical; R represents a phenyl radical optionally substituted by halogen; lower alkyl, lower alkoxy or hydroxy, a cycloalkyl radical of 5 to 7 carbon atoms or a lower alkyl radical; R¹ represents hydrogen or lower alkyl radical;

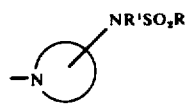

represents a ring system of formula

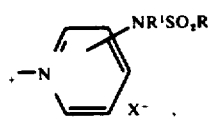
II(a)

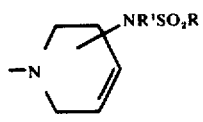
II(b)

or 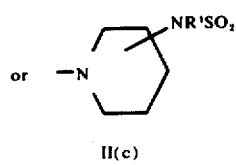
II(c)

and X⁻ represents an anion; or a pharmaceutically acceptable acid addition or quaternary ammonium salt of a compound containing ring system II(b) or II(c). Preferred compounds of the invention are those wherein —NR¹SO₂R is in the 4-position.

By the term "lower" used in connection with the groups alkyl or alkylene is meant an alkyl or alkylene group having one to six carbon atoms, preferably 1 to 4 carbon atoms, and includes both straight and branched chains.

Examples of W are unsubstituted phenyl or phenyl substituted by one or more groups, which may be the same or different selected from fluorine, chlorine, bromine, methyl, ethyl, propyl, butyl, methoxy, ethoxy, propoxy, butoxy or hydroxyl. Further examples of W are indolyl, e.g. indol-3-yl, which may be unsubstituted or substituted as described above for the substituted phenyl group W. Examples of A are methylene, ethylene, propylene, butylene, oxo-ethylene, oxo-propylene, hydroxyethylene and hydroxypropylene. Examples of R¹ are hydrogen, methyl, ethyl, propyl and butyl. Examples of R are cyclopentyl, cyclohexyl, cycloheptyl, methyl, ethyl, propyl, butyl, phenyl and phenyl substituted by the same radicals as mentioned above for the radical W when phenyl. Examples of acid addition salts are those formed from inorganic and organic acids in particular pharmaceutically acceptable acid addition salts such as the sulphate, hydrochloride, hydrobromide, hydro-iodide, nitrate, phosphate, sulphonate (such as the methanesulphonate and p-toluene-sulphonate), acetate, maleate, fumarate, tartrate and formate. Examples of X⁻ are halogen anions, e.g. the chloride and bromide ions. Examples of quaternary ammonium salts are those formed with lower alkyl halides, e.g. methyl bromide or benzyl halides.

The compounds of formula Ia as defined above possess hypotensive activity, for example as demonstrated by a standard procedure involving tests on warm blooded animals. For example, the representative compounds of fromula Ia, 3-[2-(4-benzenesulphonamido-1-piperidyl)ethyl]-indole and 4-benzenesulphonamido-1-(4-phenyl-4-oxobutyl)-piperidine both exhibited hyptensive activity when administered intravenously to normotensive rats at a dose level of 6.4 mpk. Compounds of formula I wherein

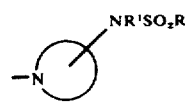

represents a pyridine or tetrahydropyridine ring system of formula II(a) or II(b) respectively are useful as intermediates for preparing compounds of formula Ia.

Particularly preferred compounds of this invention within the scope of formula Ia are compounds of general formula

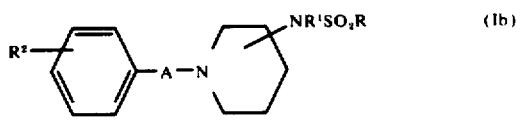
(Ib)

and pharmaceutically acceptable acid addition or quaternary ammonium salts thereof, wherein R is phenyl which may be substituted by halogen, lower alkyl, lower alkoxy or hydroxy; R¹ represents hydrogen or lower alkyl, R² represents hydrogen, halogen, lower alkyl, lower alkoxy or hydroxy; and A represents a lower alkylene, oxo lower alkylene or hydroxy lower alkylene radical; and compounds of general formula

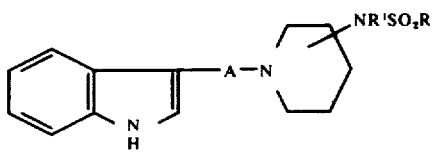 (Ic)

and pharmaceutically acceptable acid addition or quaternary ammonium salts thereof, wherein R represents a phenyl radical which may be substituted by halogen, lower alkyl, lower alkoxy or hydroxy; $R^1$ represents hydrogen or lower alkyl; and A represents lower alkylene, oxo lower alkylene or hydroxy lower alkylene.

This invention also provides processes for preparing the compounds of general formula I.

One such process for preparing compounds of formula I as defined above wherein

represents a ring system of formula II(a) or II(c) comprises reacting a compound of formula

 (III)

wherein W, $R^1$ and A are as defined above and

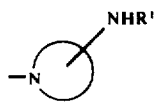

represents a ring system of formula

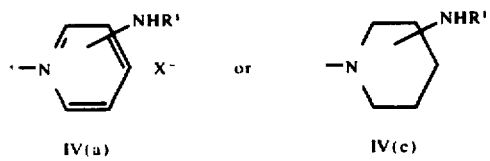

IV(a)        IV(c)

wherein $X^-$ as hereinbefore defined, with a reactive derivative of a sulphonic acid compound of formula

HOSO$_2$R         (V)

wherein R is as hereinbefore defined. As examples of reactive derivatives of the acid of formula V used in the process described above mention is made of the halide, for example the chloride or bromide, and the anhydride. Preferably the reactive derivative is the chloride. The reaction is conveniently carried out under basic conditions, for example in the presence of a tertiary amine, e.g. triethylamine, or an alkali metal hydroxide, e.g. sodium hydroxide.

The compounds of formula III may be prepared according to processes described in U.K. Pat. Nos. 1,218,570 and 1,345,872.

A further process for preparing compounds of formula I as defined above comprises reacting a compound of general formula

 (VI)

wherein W and A are as defined above and Y represents a halogen, or an equivalent replaceable radical for example an organic sulphonyl radical such as a tosyl radical, with a compound of formula

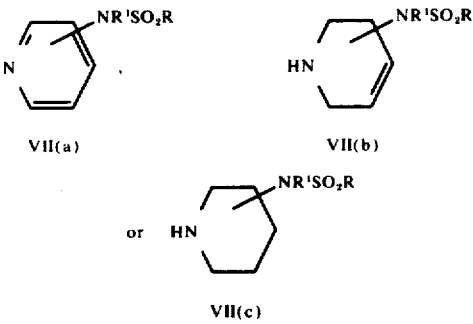

VII(a)        VII(b)

VII(c)

wherein R and $R^1$ are as hereinbefore defined. When a compound of formula VI is reacted with a compound of formula VII(a) according to the above then the radical Y becomes the anion $X^-$ in the compound of formula I produced.

Compounds of formula VI used as starting materials in the above mentioned process are known compounds or may be prepared by known methods. Compounds of formula VII(a), VII(b) and VII(c) can generally be prepared by sulphonylating a corresponding amino compound of formula

 (VIII)

and if necessary reducing the ring system to the corresponding tetrahydropyridine or piperidine ring.

Yet a further process for preparing compounds of formula I wherein

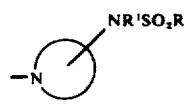

represents a ring system of formula II(b) and II(c) as defined above comprises selectively reducing a compound of formula I wherein

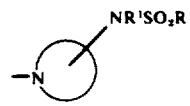

represents a ring system of formula II(a) or II(b) as defined above, as the case may be. For example mild reduction of a compound of formula I having a pyridinium ring with an alkali metal borohydride, e.g. in methanol gives the tetrahydropyridine ring system of formula II(b). Under more vigorous reducing conditions, e.g. refluxing in isopropyl alcohol, use of an alkali metal borohydride gives the pyridine ring system of formula II(c).

Similarly catalytic hydrogenation of a compound of formula I having a pyridinium ring, for example in the presence of Raney nickel or a platinum catalyst gives the piperidine ring of formula II(c).

If a compound of formula I is prepared in which

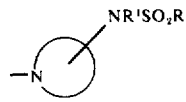

represents the tetrahydropyridine ring system of formula II(b), this may also be reduced in like manner to the piperidine ring system of formula II(c).

If a compound of formula I is prepared in which the chain A contains a carbonyl function, then this chain may be selectively reduced. For example, when A is the —CO-CH$_2$— residue this may be reduced with an alkali metal borohydride to give the

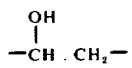

residue. When the residue is reduced under more drastic conditions, the ethylene chain —CH$_2$-CH$_2$— results.

A still further process for preparing compounds of formula I wherein A is a lower alkylene radical and

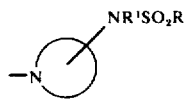

represents a ring system of formula II(b) or II(c) comprises reacting a compound of formula $$W-A-OH \qquad (IX)$$

wherein W is as hereinbefore defined and A is a lower alkylene radical, with a compound of formula VII(c) or VII(b) (in which R$^1$ and R$^2$ have the meanings defined immediately above).

The reaction is preferably carried out in the presence of a catalyst, for example Raney Nickel. An organic solvent, which is inert under the reaction conditions, is usually used, for example xylene, toluene or benzene. Preferably the reaction is carried out by heating the reactants under reflux in a water immiscible organic solvent, for example xylene, and removing the water formed during the reaction by azeotropic distillation. If necessary, reactive substituent groups can be blocked during a reaction and released later.

If necessary, in any of the reactions hereinbefore described, reactive substituent groups may be blocked during a reaction and released at a later stage. As already indicated the novel tetrahydropyridine and piperidine compounds provided by the invention contain a basic nitrogen atom and thus can form acid addition salts with acids (particularly pharmaceutically acceptable salts) or quaternary ammonium salts, for example with alkyl halides or aralkyl halides (particularly methyl iodide or benzyl chloride or bromide). The acid addition salts may either be formed in situ during the hereinbefore described processes and isolated therefrom or a free base may be treated with the appropriate acid in the presence of a suitable solvent and then the salt isolated. The quaternary salts may be prepared by treating the free base with the appropriate halide in the presence or absence of a solvent.

A further aspect of this invention is the provision of a pharmaceutical composition comprising a compound of formula I as defined above wherein

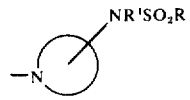

represents a ring system of formula II(c) or a pharmaceutically acceptable salt thereof together with a pharmaceutically acceptable carrier.

Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly catchets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finelydivided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be in packaged composition, the package containing specific quantities of compositions, for example packeted powders or vials or ampoules. The unit dosage form can be a capsule, catchet or tablet itself, or it can be the appropriate number of any of these in packaged form. The quantity of active ingredient in a unit dose of composition may be varied or adjusted from 5 mg. of less to 500 or more, according to the particular need and the activity of the active ingredient. The invention also includes the compounds in the absence of carrier where the compounds are in unit dosage form.

The following non-limiting Examples illustrate the invention:

EXAMPLE 1

3-[2-(4-Benzenesulphonamido-1-piperidyl)ethyl]indole

To a stirred solution of 3-[2-(4-amino-1-piperidinyl)ethyl]indole monohydrate (0.522 g., 0.002 mole) and triethylamine (1 ml.) in methylene chloride (10 ml.) was added dropwise a solution of benzenesulphonyl chloride (0.354 g., 0.005 mole) in methylene chloride (5 ml.). The mixture was stirred for 18 hours at ambient temperature and then washed with water (3 × 10 ml.). The separated organic phase was dried ($MgSO_4$) and evaporated to give an oil (0.933 g). Treatment of this with ethanol/HCl until acid, then ethyl acetate and diethyl ether afforded the title compound as the monohydrochloride quarter hydrate, colourless crystals (0.589 g.), m.p. 230.6° C.

Found: C, 59.40; H, 6.33; N, 9.56. $C_{21}H_{25}N_3O_2S.HCl.¼; H_2O$ requires: C, 59.42; H, 6.29; N, 9.90%.

EXAMPLE 2

4-Benzenesulphonamido-1-(4-phenyl-4-oxobutyl)-piperidine

To a stirred solution of 4-amino-1-(4-phenyl-4-oxobutyl)-piperidine dihydrochloride (1.752 g. 0.005 mole) and triethylamine (2 ml.) in $CH_2Cl_2$ (10 ml.) was added dropwise a solution of benzenesulphonyl chloride (0.883 g. 0.005 mole) in $CH_2Cl_2$(5 ml.). The mixture was stirred for 24 hours and extracted with water (3 × 10 ml.). The organic phase was separated, dried ($MgSO_4$) and evaporated to give a crystalline residue. Treatment of this with ethanolic HCl followed by diethyl ether afforded the title compound as the monohydrochloride, buff solid (1.961 g.), m.p. 195.2° C.

Analysis - Found: C, 59.69; H, 6.68; N, 6.49; $C_{21}H_{26}N_2SO_3.$ HCl requires: C, 59.64; H, 6.44; N, 6.63%.

EXAMPLE 3

N-(1-[2-(Indole-3-yl)ethyl]-4-piperidyl)methanesulphonamide

To 3-[2-(4-Amino-1-piperidyl)ethyl]indole (1.307 g.) suspended in a solution of triethylamine (2 mls.) in dichloromethane (10 mls.) at room temperature with stirring was added methane sulphonyl chloride (0.570 g.) in dichloromethane (5 mls.). After stirring for 18 hours the solution was washed with water and the organic phase separated, dried and evaporated to yield the title compound (1.690 g.) as an oil. This was recrystallised from ethanolic hydrogen chloride as the hydrochloride salt (0.560 g., m.p. 241°–242° C).

$C_{16}H_{23}N_3O_2S.HCl$ requires C, 53.69; H, 6.76; N, 11.74%; Found: C, 53.69; H, 6.85; N, 11.78%.

EXAMPLE 4

4-Methanesulphonamido-1-(4-phenyl-4-oxobutyl)-piperidine

4-Amino-1-(4-phenyl-4-oxobutyl)piperidine (1.23 g. 0.005m) was suspended in a solution of dichloromethane (10 mls) containing triethylamine (2 mls). Methanesulphonyl chloride (0.570 g, 0.005 m) in dichloromethane (5 mls) was added dropwise over 5 minutes and the reaction stirred overnight at room temperature. The solution was then washed with five aliquots of water and dried over magnesium sulphate. Evaporation yielded the free base in 90% purity. This was triturated in ethyl acetate and warmed. The mother liquor was decanted off and evaporated to yield the title compound m.pt 141.4° C. This was recrystallised from ethanolic HCl as the hydrochloride salt (0.510g), m.pt 167.4° C.

$C_{16}H_{24}N_2O_3S.HCl.¼H_2O$ requires C, 52.59; H, 7.04; N, 7.69%; Found: C, 52.37; H, 6.78; N, 7.67%.

EXAMPLE 5

3-[2-(4-p-Chlorobenzenesulphonamido-1-piperidyl)ethyl]indole

Using an analogous procedure to Example 1 3-[2-(4-amino-1-piperidyl)ethyl]indole monohydrate may be reacted with p-chlorobenzenesulphonyl chloride to give the title compound.

EXAMPLE 6

3-[2-(4-p-Toluenesulphonamido-1-piperidyl)ethyl]indole

Using an analogous procedure to Example 1 3[2-(4-amino-1-piperidyl)ethyl]indole monohydrate may be reacted with p-toluenesulphonyl chloride to give the title compound.

EXAMPLE 7

3-[2-(4-Cyclohexanesulphonamido-1-piperidyl)ethyl]indole

Using an analogous procedure to Example 1 3-[2-(4-amino-1-piperidyl)ethyl]indole monohydrate may be reacted with cyclohexanesulphonyl chloride to give the title compound.

EXAMPLE 8

3-[2-(4-m-Methoxybenzenesulphonamido-1-piperidyl)-ethyl]indole

Using an analogous procedure to Example 1 3-[2-(4-amino-1-piperidyl)ethyl]indole monohydrate may be reacted with m-methoxybenzenesulphonyl chloride to give the title compound.

EXAMPLE 9

4-Benzenesulphonamido-1-(4-p-chlorophenyl)4-oxobutyl)-piperidine

Using an analogous procedure to Example 2 4-amino-1-(4-p-chlorophenyl-4-oxobutyl)piperidine may be reacted with benzenesulphonyl chloride to give the title compound.

EXAMPLE 10

4-Benzenesulphonamido-1-(4-p-hydroxyphenyl-4-oxobutyl)-piperidine

1-Chloro-4-(p-hydroxy)phenyl-4-oxo-n-butane may be reacted with 4-benzenesulphonamidopiperidine in the presence of potassium carbonate to give the title compound.

EXAMPLE 11

4-Cyclohexanesulphonamido-1-(4-phenyl-4-oxobutyl)piperidine

Using an analogous procedure to Example 2 4-amino-1-(4-phenyl-4-oxobutyl)piperidine may be reacted with cyclohexanesulphonyl chloride to give the title compound.

EXAMPLE 12

4-Benzenesulphonamido-1-[3-(3-indolyl)-4-oxobutyl]-piperidine

Using an analogous procedure to Example 2 4-amino-1-[4-(3-indolyl)-4-oxobutyl]piperidine may be reacted with benzenesulphonyl chloride to give the title compound.

EXAMPLE 13

4-Benzenesulphonamido-1-(4-phenyl-4-hydroxybutyl)-piperidine

4-Benzenesulphonamido-1-(4-phenyl-4-oxobutyl)-piperidine prepared according to Example 2 may be reduced using sodium borohydride to give the title compound.

EXAMPLE 14

3-{2-[4-(N-Methyl)benzenesulphonamido-1-piperidyl]ethyl}-indole

Using an analogous procedure to Example 1 3-{2-[4-(N-methyl)amino-1-piperidyl]ethyl}indole may be reacted with benzenesulphonyl chloride to give the title compound.

EXAMPLE 15

4-Benzenesulphonamido-1-(4-phenylbutyl)piperidine

4-Benzenesulphonamido-1-(4-phenyl-4-oxobutyl)-piperidine may be reacted with hydrazine hydrate and potassium hydroxide under Wolff-Kishner reaction conditions to give the title compound.

EXAMPLE 16

4-(p-Chlorobenzenesulphonamido)1-(4-phenyl-4-oxobutyl)piperidine

Using an analogous procedure to Example 2 4-amino-1-(4-phenyl-4-oxobutyl)piperidine dihydrochloride may be reacted with p-chlorobenzenesulphonyl chloride to give the title compound.

EXAMPLE 17

4-(p-Methoxybenzenesulphonamido)-1-(4-phenyl-4-oxobutyl)piperidine

Using an analogous procedure to Example 2 4-amino-1-(4-phenyl-4-oxobutyl)piperidine dihydrochloride may be reacted with p-methoxybenzenesulphonyl chloride to give the title compound.

We claim:

1. A compound having the general formula

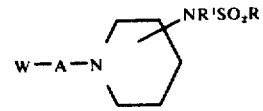

(Ia)

wherein W represents a phenyl radical, which may be unsubstituted or substituted by halogen, lower alkyl, lower alkoxy or hydroxy; A represents a lower alkylene radical, an oxo lower alkylene radical or a hydroxy lower alkylene radical; R represents a phenyl radical optionally substituted by halogen, lower alkyl, lower alkoxy or hydroxy, a cycloalkyl radical of 5 to 7 carbon atoms or a lower alkyl radical; $R^1$ represents hydrogen or a lower alkyl radical; or a pharmaceutically acceptable acid addition or quaternary ammonium salt thereof.

2. A compound as claimed in claim 1 having the general formula:

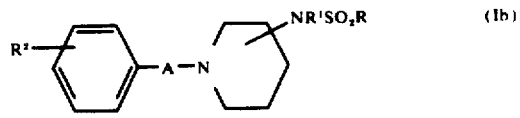

(Ib)

or a pharmaceutically acceptable acid addition or quaternary ammonium salt thereof, wherein R represents phenyl which may be substituted by halogen, lower alkyl, lower alkoxy or hydroxy; $R^1$ represents hydrogen or lower alkyl, $R^2$ represents hydrogen, halogen, lower alkyl, lower alkoxy or hydroxy; and A represents a lower alkylene, oxo lower alkylene or hydroxy lower alkylene radical.

3. A compound as claimed in claim 2 wherein A represents a $-COCH_2CH_2CH_2-$ radical.

4. A compound as claimed in claim 1 which is 4-benzenesulphonamido-1-(4-phenyl-4-oxobutyl)piperidine.

5. A compound as claimed in claim 1 which is 4-methanesulphonamido-1-(4-phenyl-4-oxobutyl)piperidine.

6. A hypotensive composition comprising a therapeutically effective amount of a compound as claimed in claim 1 or a pharmaceutically acceptable acid addition or quaternary ammonium salt thereof together with a pharmaceutically acceptable carrier.

* * * * *